US007018538B2

(12) United States Patent
Leiser et al.

(10) Patent No.: US 7,018,538 B2
(45) Date of Patent: Mar. 28, 2006

(54) USE OF A COMPOSITE POLYMER-COATED SORBENT FOR SEPARATION, PURIFICATION, DESALTING AND CONCENTRATION OF BIOPOLYMERS

(75) Inventors: Robert-Matthias Leiser, Solingen (DE); Lutz Plobner, Erkrath (DE); Elena Markovna Yaroshevskaya, Köln (DE); Vitali Pavlovich Zubov, Moskau (RU); Dmitry Valerievich Kapustin, Moskau (RU); Elena Jurievna Yagudaeva, Moskau (RU)

(73) Assignee: NextTec GmbH, Leverkusen (DE)

( * ) Notice: Subject to any disclaimer, the term of this patent is extended or adjusted under 35 U.S.C. 154(b) by 0 days.

(21) Appl. No.: 10/936,723

(22) Filed: Sep. 9, 2004

(65) Prior Publication Data
US 2005/0098501 A1 May 12, 2005

Related U.S. Application Data

(63) Continuation of application No. 09/959,321, filed as application No. PCT/EP00/03674 on Apr. 25, 2000, now abandoned.

(30) Foreign Application Priority Data

Apr. 23, 1999 (EP) .................................. 99108029
Aug. 26, 1999 (EP) .................................. 99116675

(51) Int. Cl.
*B01D 15/08* (2006.01)
(52) U.S. Cl. .................... 210/635; 210/656; 210/198.2; 536/25.4
(58) Field of Classification Search ................. 210/635, 210/656, 659, 198.2, 502.1; 536/25.4
See application file for complete search history.

(56) References Cited

U.S. PATENT DOCUMENTS

| | | | | |
|---|---|---|---|---|
| 3,933,717 | A | * | 1/1976 | Shinohara et al. .......... 524/567 |
| 4,200,726 | A | * | 4/1980 | Ishii et al. .................... 528/99 |
| 4,292,417 | A | * | 9/1981 | Ishii et al. ................... 525/510 |
| 4,814,077 | A | * | 3/1989 | Furuyoshi et al. .......... 210/266 |
| 5,176,851 | A | | 1/1993 | Barry, Jr. .................... 252/500 |
| 5,225,495 | A | * | 7/1993 | Han et al. ................. 525/327.4 |
| 5,232,631 | A | | 8/1993 | Cao et al. ................... 252/500 |
| 5,281,363 | A | * | 1/1994 | Shacklette et al. .......... 252/500 |
| 5,972,692 | A | * | 10/1999 | Hashimoto et al. ...... 435/285.2 |
| 6,265,615 | B1 | * | 7/2001 | Kaner et al. ................ 564/424 |
| 6,468,785 | B1 | * | 10/2002 | Wang et al. ............. 435/287.2 |

FOREIGN PATENT DOCUMENTS

| | | | |
|---|---|---|---|
| EP | 0321 703 A1 | 11/1988 | .............. 210/502.1 |
| WO | WO 89/07265 | 8/1989 | .............. 210/502.1 |
| WO | WO 89/11648 | 11/1989 | .............. 210/502.1 |
| WO | WO 94/00215 | * 1/1994 | .............. 210/502.1 |

OTHER PUBLICATIONS

Fasorng et al. "Study of the Crystallinity of Polyaniline". Mol. Cryst. Liq. Cryst., 16 (1988), 175-84.
Hu et al., "Electrically Conducting Polyaniline-Poly(acrylic acid) Blends". Polymer International, 45 (1998), 262-70.
Kobryanski et al., "Izutchenie mechanizma reakcii kondensatcii anilina na primere polutcheniya vodorastvorimogo polimera" Vysokomolekulyarnye soedineniya, A: 37 (1995), 35-38.
Nicolau, Y.F. et al., "XPS characterization of polyaniline filled n+-type porous silicon." Synthetic Metals, 71 (1995), 2073-74.
Shevchenko, V.V. et al., Electron Microscopy and X-ray Diffraction Studies of Polyaniline Films. Synethetic Metals, 37 (1990), 69-71.
Sindhimeshram, D.C., Transport properties of substituted derivatives of poly(aniline). Indian Journal of Chemistry, 34A (1995), 260-67.
Syed, A. Et al., "Polyaniline: Reaction Stoichiometry and Use as an Ion-Exchange Polymer and Acid/Base Indicator." Synthetic Metals, 36 (1990), 209-15.
Tassi, Eliana et al., "A Conductive and Electroactive Elastomer: A Polyaniline-Nitrilic Rubber Composite", J. Chem. Soc., Chem. Commun. (1990), 155-56.
Vincent, Brian et al., "Colloidal Dispersions of Electrically-conducting, Spherical Polyaniline Particles", J. Chem. Soc., Chem. Commun. (1990), 683-84.
Wu, Shuizhu. "Diffusion-controlled Deposition of Polyaniline onto Poly(methyl methacrylate) Substrates." Polymer International, 47 (1998), 335-39.
Abstract of Japan Patent No. 02-004446 Jan. 9, 1990.

* cited by examiner

*Primary Examiner*—Ernest G. Therkorn
(74) *Attorney, Agent, or Firm*—Jacobson Holman PLLC

(57) ABSTRACT

Use of a composite sorbent having an at least partial coating on a support, which coating comprises essentially polyanilines or derivatives of polyanilines for the separation, isolation, identification, purification and/or detection of biomolecules in particular nucleic acids, proteins, polysaccharides in analytical or preparative scale.

8 Claims, No Drawings

USE OF A COMPOSITE POLYMER-COATED SORBENT FOR SEPARATION, PURIFICATION, DESALTING AND CONCENTRATION OF BIOPOLYMERS

REFERENCE TO RELATED APPLICATIONS

This application is a continuation of Ser. No. 09/959,321, filed Jan. 24, 2002, now abandoned and a 371 of PCT/EP00/03674 filed Apr. 25, 2000.

The invention is concerned with the use of a composite sorbent comprising a support, which is at least partially covered by a polymeric film based on primary aromatic amines [D. Sindhimeshram et al. "Transport Properties of Substituted Derivatives of Polyaniline", Electron Manuf. and Test", 260–267(1995)]. The inner surface of the porous supports is also covered. The composite sorbent of the invention is prepared by conditions, which are disclosed as well. A chromatographic column or cartridge is also disclosed.

A lot of different chromatographic materials are known for the separation of various substances. These chromatographic supports can be used alone or in combinations to cover almost all specific needs. However, it is still necessary to get new sorbents for the separation of biomolecules such as nucleic acids with other characteristic features.

U.S. Pat. No. 5,225,495 discloses a process for, forming polyaniline films on a substrate and to composite articles formed by that process. These materials are used for these films which are electrically conductive.

JP 02004446 discloses the gas adsorbent comprising an electroconductive polymer having conjugated double bonds. The conductive polymer is deposited on the surface of a power support. The surface includes micropore walls. Polyaniline is used as the electric conductive polymer.

The technical problem underlying the present invention is to provide a method by which proteins and other substances, can be separated from nucleic acids and which, therefore, is particular useful for fast one-step sample preparation of DNA, e.g. for PCR. A sorbent with mentioned properties is subject of EP 99 100 416. But this sorbent has one disadvantage: the polymeric surface is hydrophobic. It is desired, that the separation addressed above can be performed in aqueous environment.

The technical problem is solved by the use of a composite sorbent having an at least partial coating on a support, which coating comprises essentially polyanilines or derivatives of polyanilines for the separation, isolation, identification, purification and/or detection of biomolecules in particular nucleic acids, porteins, polysaccharides in analytical or preparative scale.

Preferably the support is an inorganic material selected from the groups comprising inorganic metal oxides preferably with a porous structure such as oxides of aluminium, titanium, zirconium, silicon and/or iron.

In a further embodiment of the invention the support is an organic material preferably with a porous structure such as linear or cross-linked polystyrene, polyethylene, polyacrylate particles or surfaces.

The derivatives of polyaniline are preferably substituted or nonsubstituted alkyl anilines, aromatic systems, ethylaniline, propylanilin, and/or ethoxyanilin.

The present invention also concerns a chromatographic column, capillary or cartridge at least partially filled with a composite sorbent comprising a support which is at least partially covered by a polymeric coating comprising essentially polyanilins or derivatives of polyanilines.

The present invention pertains also to a membrane-like article comprising a composite sorbent, comprising a support which is at least partially covered by a polymeric coating comprising essentially polyanilins or derivatives of polyanilines wherein the composite sorbent is embedded in a porous polymeric or inorganic matrix.

According to the invention the use of the invention is easily performed with a kit comprising a composite sorbent comprising a support which is at least partially covered by a polymeric coating comprising essentially polyanilins or derivatives of polyanilines which composite sorbent is in loose form or packed in chromatographic columns or cartridges or a membrane-like article, optionally in combination with filter materials, reagents and/or buffers or other devices or chemicals for performing sample preparations or chromatographic separations.

Combining the high binding capacity for proteins and the porous structure of the composite sorbent DNA can be separated from other substances in one step. Beside this, the special property of polyanilins to change the colour under distinct conditions [Hailin Hu et al. "Electrically Conducting Polyaniline—Poly(acrylic acid) Blends"; *Polymer International*, 45, 262–270(1998); Ya. Kogan et al. "$(NH_4)_2IrCl_6$ *i drugie protoniruutshie agenty khimitcheskoj polimerizatcii anilina*" *Izvestiya Akademii Nauk* Ser. khim., 8, 1500–1502 (1994)] allows its use for detection of interaction of separated substances on the sorbent surface.

The main advantages of the use of the composite sorbent as suggested earlier [A. Syed et al. "Polyaniline: Reaction Sthechiometry and Use as an Ionexchange Polymer and Acid/Base Indicator"; *Synthetic Metals*, 36, 209–215(1990); U.S. Pat. No. 5,281,363; 1/1994, Shacklette et al.; 252/500; U.S. Pat. No. 5,232,631; 8/1993, Yong Cao et al.; 252/500; 3. Nicolau "Characteristic of Polyaniline filled by Porouse $n^+$-type Silica by the Renthgene Photoelectrical Specthroscopy Method"; *Synthetic Metals*, 1–3, 2073–2074(1995)] are the ease of handling, the speed of the separation process and the possibility of a visual control of sorption and separation processes. DNA is contained in the flow-through (cartridge methods) or in the supernatant (batch methods). Bound proteins can be eluted separately by a gradient and subsequently analysed if needed.

The composite sorbent to be used according to the invention containing a support which is at least partially covered by a chemically stable polymeric film with high affinity to the surface of the support is obtained by a process comprising the steps of:

§ preparation of a suspension by contacting a support with the reaction mixture contacting at least one or more monomers and one or more dopants (as disclosed in U.S. Pat. No. 5,281,363, incorporated by reference), § addition of an oxidizer to the prepared suspension, § polymerization of monomers on the surface of the support.

The chemically stable polymeric film is such like the one disclosed in [V. Kobryanski et al. "*Izutchenie mechanizma reaktcii kondensatcii anilina na primere polutcheniya vodorastvorimogo polimera*" *Vysokomolekulyarnye soedineniya*, A, 37, 35–38(1995).] and [Wu Shuizhu et al. "Diffusion-controlled Deposition of Polyaniline onto Poly(methylmethacrylate) Substrates"; *Polymer International*, 47, 335–339(1998); E. Tassi et al. "A Conductive and Electroactive Elastomer: A Polyaniline—Nitrilic Rubber Composite"; *J. Chem. Soc., Chem. Commum*, 155–156(1990); B. Vincent et al. "Colloidal Dispersions of Electrically-conducting, Spherical Polyaniline Particles"; *J. Chem. Soc., Chem. Commun*, 683–684(1990); U.S. Pat. No. 5,176,851; 1/1993, Barry et al.; 252/500; V. Shevchenko et al. "Electron Microscopy and X-Ray Difraction Studies of Polyaniline Films"; *Synthetic Metals*, 37, 69–71(1990)] respectively.

Porous or nonporous inorganic materials selected from the group comprising inorganic metal oxides such as oxides of aluminium, titanium, zirconium, silicon and/or iron as well as porous or nonporous organic materials such as linear or cross-linked polystyrene, polyethylene and polyacrylate particles or surfaces can be used as support of the composite sorbent to be used in the invention. Particularly preferred is porous glass, e.g. controlled pore glass (CPG). Typically, CPG with a pore size in the range of 10 to 200 nm is used.

The formation of the polyaniline film on the support's surface is carried out under conditions ensuring the formation of a solid [C. Fasomg et al. "Study on the Crystallinity of Polyaniline", *Mol. Cryst. Liq. Cryst.,* 160; 175–184 (1988)], stable layer of unbranched polymer molecules. The support material is filled into a reaction vessel and preferably set under vacuo. A water-based or organic solvents containing reaction mixture is then successively introduced into the reaction vessel and contacted with the support material. The reaction mixture may contain one or more substituted or unsubstituted aniline monomers doped with one or more dopants.

To carry out the polymerization preferably an aqueous solution of oxidizer, particularly ammonium persulfate, potassium persulfate, sodium vanadate, peroxydisulfate, dicumylperoxide, alkylhydroperoxide is added and the system is incubated for 1 to 3 h at −5° C. to 25° C. After incubation, the inner and outer surface of porous inorganic material is covered by polyaniline or derivatives. Unreacted components are removed by filtration, the sorbent is washed and then dried under vacuo.

The composite sorbent to be used according to the invention can be used for separation of biomolecules such as nucleic acids, proteins and polysaccharides. Therefore, a chromatographic column or cartridge is filled with composite sorbent. The composite sorbent behaves similar to other solid chromatographic supports so that the methods for filling chromatographic columns or cartridges can be used in an analogous manner. The composite sorbent can also be prepared in the form of a membrane-like item comprising the composite material of the invention wherein the composite sorbent is embedded in a porous polymeric or inorganic matrix.

For easy use it is advantageous to provide the invented composite material in a loose form, prepacked into a chromatographic column or cartridge or as a membrane-like item in combination with filter materials, reagents and/or buffers or other devices or chemicals needed for performing sample preparation and chromatographic separations, e.g. in form of a kit.

The chromatographic separation is not limited in its scale. It can be used in any chromatographic operation for separation, isolation, identification, purification and/or detection of biomolecules, in particular nucleic acids, in preparative or analytical scale.

The invention is further explained in the following examples, which are understood to be not limiting.

EXAMPLE 1

An amount of 2.5 to 15 g of the porous support (e.g. controlled pore glass) with an averaged pore diameter from 10 to 200 nm and a medium specific surface area from 30 to 130 $m^2/g$ is transferred to a glass ampoule (reaction vessel). The ampoule is connected to a vacuum source and via a valve to a reservoir containing 30 ml of an aqueous solution of the monomers (1–4 $\mu l/m^2_{CPGsurface}$) and dopant (HCl) in molar ratio of 1:3. A vacuum of 10 mbar is applied to the ampoule. When the support particles stopped moving (after approx. 20 min.) the monomer-containing solution is filled into the ampoule from the bottom while the line to the vacuum source is closed. During this step the monomer solution is wetting the support and penetrating into the pores of the support particles. Now the valve to the monomer reservoir is closed. The next step has to be carried out as quick as possible. Under atmospheric pressure 20 ml of an oxidizer solution (0,005–0.008 g/1 $m^2_{CPGsurface}$) are added into the ampoule under mixing. The mixing is continued at 20° C. for 0.5–3 h.

After the first 10–15 min the suspension colour becomes dark-blue. At the end of the process the colour of the suspension changes to dark-green. The product is removed from the ampoule and then washed with water (40 ml per gram) and then incubated in 1 M ammonium hydroxide (20 ml per gram) for 3 h. The colour of the composite sorbent becomes dark-blue. After that the sorbent is extensively washed with 50%-Vol Methanol in water (100 ml per gram) and dried at 60° C. in a vacuum oven for 17 h.

EXAMPLE 2

10 g of surface area 33 $m^2/g$, NPO "GORKOVKIY Khimitcheskiy Zavod", Nigniy Novgorod, Russia) are filled into an ampoule and evacuated for 20 min. First, an aqueous solution of monomers with dopant (HCl) (0.924 ml of aniline per g support) is added and then a solution of oxidizer (0226 g ammonium persulfate per g MPS-support). All steps are carried out as in example 1. The reaction continues for 2 h. under stirring.

After reaction the sorbent is transferred into a funnel with a glass filter disc and washed with 0.4 L of water and incubated in 0.2 L of ammonia hydroxide for 3 h. After that the product is washed with 0.8 L of water on the funnel with a glass filter disc and dried at 60° C. in a vacuum oven for 17 h. The colour of the product is dark-blue.

EXAMPLE 3

The coating is carried out analogous to the method described above in Example 2. The time for reaction is 3 h.

Support: 10 g MPS-2000 GC (medium pore size 200 nm, medium specific surface area 33 $m^2/g$, NPO "GORKOVKIY Khimitcheskiy Zavod", Nigniy Novgorod, Russia).

Amount of aniline in water: 0.93 ml/g support.

EXAMPLE 4

The procedure is as in Example 3.

Support: 10 g MPS-1150 GC (medium pore size 100 nm, medium specific surface area 39 $m^2/g$, NPO "GORKOVKIY Khimitcheskiy Zavod", Nigniy Novgorod, Russia). Amount of aniline in water: 1.1 ml/g support.

EXAMPLE 5

The procedure is as in Example 3.

Support: 10 g MPS-250 GC (medium pore size 24 nm, medium specific surface area 34 $m^2/g$, NPO "GORKOVKIY Khimitcheskiy Zavod", Nigniy Novgorod, Russia).

Amount of aniline in water: 0.95 ml/g support.

EXAMPLE 6

The procedure is as in Example 3.
Support: 10 g CPG-10-240 (Fluka, medium pore size 24.2 nm, medium specific surface area 88.1 m$^2$/g).
Amount of aniline in water: 2.47 ml/g support.

EXAMPLE 7

The procedure is as in Example 3.
Support: 10 g CPG-10-500 (Fluka, medium pore size 52 nm, medium specific surface area 48.6 m$^2$/g).
Amount of aniline in water: 1.36 ml/g support.

EXAMPLE 8

The procedure is as in Example 3.
Support: 10 g CPG-10-1000 (Fluka, medium pore size 97.2 nm, medium specific surface area 37.9 m$^2$/g).
Amount of aniline in water: 1.06 ml/g support.

EXAMPLE 9

An amount of 0.3–0.5 g sorbent in TE-buffer (0.02 M Tris-HCl, pH 7.5, 1 mM EDTA) is degased for 0.5 h and the mixture is transferred into a cartridge and equilibrated with at least 20 vol. TE-buffer. 200 µl of a sample which contains the plasmid pBR 322, RNA and proteins in TE-buffer are transferred onto the cartridge. The cartridge is eluted with TE-buffer and 200 µl-fractions of the eluate are collected. The purified DNA is contained in the first fraction as can be shown spectrophotometrically and by gel electrophoresis (0.8% agarose gel). RNA and proteins can be eluted with 500/% methanol.

EXAMPLE 10

The composite sorbent is prepared as in Example 9 and filled into a column (length 10 cm, inner diameter 4 mm). A sample of 200 µl containing 2 mg pBR 322, RNA and proteins is transferred onto the column and separated chromatographically (flow rate 0.5 ml/min).
The eluent is a A-B-gradient:
A: 10 mM Tris-HCl pH 7.5
B: A+isopropanole
0–5 min: 100% A, 0% B
5–12.5 min: 80% A, 20% B
12.5–20 min: 0% A, 70% B The mechanical stability of the sorbent due to the mechanical properties of the inorganic support offers the possibility for use as fillings in cartridges and columns and for purifications in a batch format (particle suspension).

Testing of the Sorbents

1 Mercury Porometry

The porogrammes obtained by testing the sorbents based on MPS-2000, MPS-1150 and MPS-250 show an even distribution of the pores depending on the pore size of the starting material. The medium coating thickness of the polymeric layer is 50–75 Å.

§Determination of the Hydrolytic Stability

Samples of the sorbent based on polyaniline-coated MPS and a sample of the non modified MPS were incubated for 16 h under basic conditions (pH 11) and centrifugated (3000 rpm, 1 min). Aliquots of the supernatant were taken and mixed with a solution of ammonia molybdate and sulphuric acid. Spectra were recorded from these mixtures. A peak at I=320 nm indicates the presence of silicamolybdanic acid, formed when silicon ions are resolved from the particles under basic conditions. Non modified support particles showed the highest peak. The smallest peaks referred to the those surface-modified particles which had been coated for 3 h. The hydrolytic stability of these sorbents was increased to the 2.5- to 21 fold.

The described modified sorbents (based on MPS-250 GC, MPS-1150 GC, MPS-2000 GC and CPG-10-500) were used for the purification of genomic DNA from lysates of *Escherichia coli*.

1 An overnight culture was made from the strain *E. coli* JM 109 (50 µl bacteria cells, 10 ml medium, 37° C.).
2 From this culture 1 ml was centrifugated in micro centrifuge tubes.
3 After removal of the supernatant the bacterial pellet was suspended in 100 µl buffer 1 (2 mg/ml lysozyme, 2 mM CaCl$_2$, 100 mM Tris-HCl pH 7.9, 4% succrose).
4 For cell lysis the suspension was incubated for 8 min at 60° C.
5 100 µl buffer 2 were added (1% MIRA Tensid-Mix, 1.5 mM EDTA) and cooled to room temperature.
6 The mixture was shaken 10 min at room temperature and incubated for further 5 min without shaking at room temperature.
7 The mixture was centrifuged for 2 min at 13,000 rpm.
8 The supernatant was given onto a sorbent-packed column and eluted with TE-buffer.

Preparation and Use of the Sorbent

The sorbent is subsequently wetted in methanol, 50% methanol and water and then degassed for 0.5 h. The supernatant is decanted and the sorbent washed 4 times with TE buffer. While stirring the sorbent in TE buffer it is degassed under vacuo in an exciccator. Cartridges are packed with this suspension of the sorbent (120 mg/ml).

A bacterial lysate (see above, step 8) from 1 ml of overnight culture is prepared and pipetted onto the cartridge and eluted with TE buffer. The cartridge is incubated 5–10 min without elution. Five fractions with volume of 200 µl are collected immediatly after the cartridge starts to drop. The fractions are further analysed by agarose gel electrophoresis (0.80/% agarose in 89 mM Tris; 89 mM boric acid; 2 mM EDTA) at a constant current of 0.100 mA.

Gels are stained with ethidium bromide. Genomic DNA but not RNA is found in the second fraction. The DNA contaning fraction is measured in a spectrophotometer. The ratio of the absorption $A_{260}$:$A_{280}$ of such fractions is in the range of 1.58 to 1.78.

What is claimed is:

1. A method for separation, isolation, identification, purification and/or detection of nucleic acids in analytical or preparative scale comprising (i) filling, at least partially, a chromatographic column, capillary, or cartridge with a composite sorbent comprising a support at least partially covered by a polymeric coating, the coating comprising polyaniline or derivatives of polyaniline, (ii) applying a sample containing nucleic acids and other substances to the composite sorbent, and (iii) eluting the nucleic acids, separated from the other substances, from the composite sorbent, without utilizing the electrical conductivity of said polyaniline or its derivatives.

2. The method according to claim 1, wherein the support is an inorganic material selected from the groups comprising inorganic metal oxides having a porous structure such as oxides of aluminum, titanium, zirconium, silicon and/or iron.

3. The method according to claim 1, wherein the support is an organic material having a porous structure such as linear or cross-linked polystyrene, polyethylene, polyacrylate particles or surfaces.

4. The method according to claim 1, wherein the derivatives of polyaniline are substituted or non-substituted alkyl anilines, aromatic systems, ethylaniline, propylaniline and/or ethoxyaniline.

5. The method according to claim 1, wherein the separation of nucleic acids from other substances is conducted in one step.

6. A method for separation, isolation, identification, purification and/or detection of nucleic acids comprising (i) applying a sample containing nucleic acids and other substances to a composite sorbent comprising a support at least partially covered by a polymeric coating, the coating comprising polyaniline or derivatives of polyaniline, and (ii) eluting the nucleic acids, separated from the other substances, from the composite sorbent, without utilizing the electrical conductivity of said polyaniline or its derivatives.

7. A method for separation, isolation, identification, purification and/or detection of nucleic acids comprising (i) applying a sample containing nucleic acids and other substances to a composite sorbent, wherein the composite sorbent is in loose form or packed in a chromatographic column or cartridge, and wherein the composite sorbent comprises a support at least partially covered by a polymeric coating, the coating comprising polyaniline or derivatives of polyaniline, and (ii) eluting the nucleic acids, separated from the other substances, from the composite sorbent, without utilizing the electrical conductivity of said polyaniline or its derivatives, said composite sorbent in loose form or packed in a chromatographic column or cartridge is provided in a kit together with filter materials, reagents, and/or buffers or other devices or chemicals, for performing sample preparations or chromatographic separations.

8. A method for separation, isolation, identification, purification and/or detection of nucleic acids comprising (i) applying a sample containing nucleic acids and other substances to a composite sorbent, wherein the composite sorbent is in loose form or a membrane-like article, and wherein the composite sorbent comprises a support at least partially covered by a polymeric coating, the coating comprising polyaniline or derivatives of polyaniline, and (ii) eluting the nucleic acids, separated from the other substances, from the composite sorbent, without utilizing the electrical conductivity of said polyaniline or its derivatives, said composite sorbent in loose form or membrane-like article is provided in a kit together with filter materials, reagents, and/or buffers or other devices or chemicals, for performing sample preparations or chromatographic separations.

* * * * *